United States Patent [19]

Arpe et al.

[11] Patent Number: 4,480,128
[45] Date of Patent: Oct. 30, 1984

[54] PROCESS FOR THE MANUFACTURE OF O-TOLUIDINE AND/OR M-TOLUIDINE AND/OR P-TOLUIDINE

[75] Inventors: Hans-Jürgen Arpe, Frankfurt am Main; Heinz Litterer, Wiesbaden, both of Fed. Rep. of Germany

[73] Assignee: Hoechst Aktiengesellschaft, Frankfurt am Main, Fed. Rep. of Germany

[21] Appl. No.: 484,179

[22] Filed: Apr. 12, 1983

[30] Foreign Application Priority Data

Apr. 15, 1982 [DE] Fed. Rep. of Germany ....... 3213876

[51] Int. Cl.$^3$ ............................................. C07C 85/26
[52] U.S. Cl. .................................................... 564/424
[58] Field of Search ......................................... 564/424

[56] References Cited

U.S. PATENT DOCUMENTS 3,069,470 12/1962 Fleck et al. ......................... 564/424
4,181,811 1/1980 Young ................................. 585/486
4,371,721 2/1983 Wu .................................. 564/424 X

OTHER PUBLICATIONS

Taniguchi et al., Toludine Isomer Separation by Selective Absorption, 1980, Chemical Abstract 92; 215042a.

Primary Examiner—Paul F. Shaver
Attorney, Agent, or Firm—Curtis, Morris & Safford

[57] ABSTRACT

The invention provides a process for the manufacture of o-toluidine and/or m-toluidine and/or p-toluidine, which comprises the two following steps (a) and (b):

(a) treatment of a toluidine isomer mixture or of the not intended toluidine isomer or of one of the not intended toluidine isomers with an isomerization catalyst selected from the group of synthetic zeolites of the pentasil type, (b) isolation of the intended isomer or one of the intended isomers from the isomer mixture formed in step (a) by selective adsorption to a medium-pore or large-pore zeolite and subsequent desorption, furthermore discharge of the isolated isomer and recycling of the remaining isomer mixture to step (a).

12 Claims, No Drawings

PROCESS FOR THE MANUFACTURE OF O-TOLUIDINE AND/OR M-TOLUIDINE AND/OR P-TOLUIDINE

The present invention provides a process for the manufacture of each of the three possible toluidine isomers, starting from one of the not intended isomers or from the not intended isomer, or from any mixture of two of them or of all three toluidine isomers, especially a mixture containing the intended isomer in an economically insufficient concentration.

o-, m- and p-toluidine (methyl aniline, aminotoluene, toluene amine) that is, $C_6H_4CH_3NH_2$ isomers, are industrially manufactured in general by reduction of the corresponding nitrotoluenes. o-, m- and p-nitrotoluene for their part are formed simultaneously in the nitration of toluene. Thus, for example, a mixture of 63% of o-nitrotoluene, 33-34% of p-nitrotoluene and 3-4% of m-nitrotoluene is obtained under usual nitration conditions, which mixture can be separated to give the pure products by a combination of distillation and crystallization according to a special method, the so-called draining (Winnacker-Küchler, Chemische Technologie 1972, vol. 4, p. 156). The quantitative ratio of the isomers can be influenced by various measures (Kirk-Othmer, Encyl. of Chemical Technology, 3rd, ed., 1978, vol. 15, p. 929); the weight proportion of the p-nitrotoluene may for example be varied from about 63 to 38%, and that of o-nitrotoluene from 34 to 58%, while variation of the m-toluene amount is strictly limited to a range of 2.3 to 4.3 weight % of the total yield of nitrotoluene. Thus, a very small amount only of m-nitrotoluene can be disposed of for the further reduction to m-toluidine. It is generally impossible to obtain a uniform nitrotoluene isomer for example by suitable selection of the catalyst or the reaction conditions. In addition to these facts there is a different demand on the market for the nitrotoluenes (as preferred starting components for the toluidines) on the one hand, and the toluidines on the other. Thus, for the different application fields of the three toluidine isomers, such as manufacture of dyestuffs, vulcanization accelerators, textile auxiliaries, there is a varying demand (depending on the market conditions) which cannot be covered in an economically optimal manner, that is, free from by-products at least temporarily undesirable and therefore unsalable.

It was therefore the object of the present invention to provide a process for the manufacture of each toluidine isomer individually, which allows to start from each of the three nitrotoluene isomers (as usual starting products of the toluidines) depending on the corresponding specific and advantageous market requirements for nitrotoluene isomers. In this respect, it would be particularly interesting to start directly from nitration mixtures of toluene in the case where they were manufactured for the purpose of being hydrogenated to toluidines, so that the additional, expensive preliminary separation of the nitrotoluenes by distillation and crystallization which was hitherto required could be omitted.

These objects are achieved by the process of the invention for the manufacture of o-toluidine and/or m-toluidine and/or p-toluidine, which comprises the two following steps (a) and (b):

(a) treatment of a toluidine isomer mixture or of the not intended toluidine isomer or of one of the not intended toluidine isomers with an isomerization catalyst selected from the group of synthetic zeolites of the pentasil type, (b) isolation of the intended isomer or one of the intended isomers from the isomer mixture formed in step (a) by selective adsorption to a medium-pore or large-pore zeolite and subsequent desorption, furthermore discharge of the isolated isomer and recycling of the remaining isomer mixture to step (a).

In the case of a suitable composition of the toluidine isomer mixture, that is, a sufficient content of the intended isomer, it is often advantageous to carry out first an adsorption/desorption for separating the amount of intended isomer contained in the starting mixture, and to isomerize subsequently.

The process of the invention allows thus to manufacture o-toluidine and/or m-toluidine and/or p-toluidine (hereinafter often abbreviated as "o", "m" or "p"); the expression "and/or" not standing for the manufacture of isomer mixtures but indicating the possibility of preparing as desired either one isomer alone, or two separate isomers or the three of them separately.

In the case where the manufacture of one isomer alone is intended, the starting material is any of the two other isomers (for example manufacture of o from m or p) or any mixture of two or the three of the isomers (for example manufacture of o from o/m, o/p, m/p or o/m/p).

In the case where two (separate) isomers are to be prepared, the starting material is the third isomer (for example manufacture of o from p and simultaneously of m from p) or any mixture of two or the three of the isomers. However, instead of the third isomer (i.e. the not intended isomer), one of the two intended isomers may be chosen, and part of it only may be converted according to the invention to the other intended isomer.

When all three isomers (separately) are intended, a mixture of two or all isomers serves as starting material. Alternatively, part of one isomer may be converted in accordance with the invention to the two other ones.

An especially important starting material is the mixture of the three toluidines obtained by nitration and subsequent hydrogenation of toluene.

To summarize: according to the invention, an individual isomer, two or all three of the isomers can be manufactured as desired, so that finally they are separately present. That means that any intended percent distribution of the three isomers can be adjusted from 0 to 100% of o, 0 to 100% of m, and 0 to 100% of p.

Isomerization reactions are usually carried out in the presence of Friedel-Crafts catalysts such as $AlCl_3$, $BF_3$, $BF_3/HF$, $H_3PO_4$, $SnCl_4$, $FeCl_3$, $SbCl_3$, $TiCl_4$ or $ZnCl_2$, optionally in combination with protonic acids. However, when using these catalysts for isomerizing toluidines in the normal temperature range of up to the boiling point of the toluidine isomers (b.p. 200°-204° C.), the isomerization activity is insufficient. Even in the presence of mineral acids, for example hydrochloric acid in a stoichiometric ratio to the toluidine used, the otherwise isomerization-active $AlCl_3$ is unfit as catalyst. It was therefore surprising to observe the high isomerization activity of zeolites, especially synthetic zeolites of the pentasil type such as ZSM-5, ZSM-8 or ZSM-b 11, which can be obtained for example according to British Pat. No. 1,567,948, or furthermore natural or synthetic zeolites of the mordenite or faujasite type.

The Si/Al ratio of the pentasils is preferably at about 25 to 2,000, that of the mordenites preferably at 5 to 100. In the case of pentasils or mordenites having an elevated aluminum content, a "modification" by treatment with mineral acids, organic acids or chelate-forming substances can partially remove the skeleton aluminum, which brings about an increase of activity.

For use in the industrial practice, the cited zeolites are given the shape of extruded strands with the aid of binders; the binder chosen having an influence on the selectivity and the life. Suitable binder materials are above all the oxides, hydroxides or hydroxychlorides of aluminum, and the oxides or hydroxides of silicon, furthermore clay materials.

The zeolites are preferably modified by converting them by ion exchange to an especially active catalytic form. Generally, mono-, bi- or trivalent cations are used for this purpose, preferably $Na^{(+)}$, $H^{(+)}$, $NH_4^{(+)}$, $Be^{2(+)}$, $Mg^{2(+)}$, $Ca^{2(+)}$, rare earth metal ions, or combinations of these elements.

Moreover, the zeolite catalysts are preferably activated as usual by calcination, which is a further mode of modification. In some cases it is advantageous to repeat ion exchange and calcination several times. Calcination is preferably carried out at 350° to 700° C., and in some cases it is advantageous for higher stabilization to calcine in the presence of steam, ammonia or mixtures thereof at temperatures of from 600° to 900° C.

Isomerization in accordance with the invention is preferably carried out in the gaseous phase; the catalyst being fixed. The temperatures are generally from 250° to 500° C., preferably 300° to 450° C. The reaction may proceed under reduced pressure as well as a pressure of up to 50 bar; normal pressure being preferred. Alternatively, other operation modes, for example a trickling phase under elevated pressure, are possible.

In addition to the toluidines, inert solvents or diluents may optionally be passed over the catalyst in order to decrease the partial pressure. Inert gases are also suitable for this purpose. Furthermore, hydrogen may be passed over the catalyst together with the toluidines in order to prevent a too rapid deactivation. The molar ratio of hydrogen to toluidine may be for example from 0.1:1 to 10:1.

When the catalyst needs to be regenerated, this is generally realized by controlled burning with oxygen-containing gases.

According to the process of the invention, the isomerization proceeds in a very selective manner. Depending on the process conditions, for example temperature and residence time, and depending on the zeolite type and the toluidine isomer or isomer mixture, a different composition of the reaction product is the result; generally, a high proportion of the isomers formed due to ortho shifting of the methyl group is obtained. For example, o-toluidine in the reaction mixture gives a large amount of m-toluidine and less p-toluidine. On the other hand, when p-toluidine is used for the isomerization, the amount of m-toluidine is again relatively large and that of o-toluidine is small. Because of the nearly identical boiling points of o-toluidine (b.p. 200°-202° C.) and p-toluidine (b.p. 200° C.) and the boiling point of m-toluidine which is only slightly higher (b.p. 204° C.), however, the isomer mixture cannot be worked up by distillation.

According to the process of the invention, the toluidines are separated by adsorption to zeolites the ions of which are exchanged differently, depending on the isomer to be absorbed. Depending on the purpose, suitable zeolites are X or Y types which contain the appropriate cations allowing separation of the intended isomer from the isomer mixture. The adsorbed isomer as intended can be desorbed subsequently; an additional organic compound being optionally used as auxiliary for the desorption.

In the case were one intended isomer is separated first, a further isomer can be isolated from the remaining mixture of the two other isomers by means of a zeolite of the X or Y type, but with other cations as used for the separation of the first isomer. Alternatively, the said mixture of the two isomers can be recycled to the isomerization step (a), that is, in the case where the obtention of only one of the three isomers is intended. In this latter case, the mixture of the three isomers is completely converted to one single isomer by suitable repetition of steps (a) and (b). The decision for one of the various operation modes depends exclusively on the intended industrial utilization of the toluidines as intermediates for the above application fields.

The special advantage of the process of the invention resides therefore in the fact that for the first time it has become possible to convert toluene practically quantitatively to any pure toluidine isomer intended via the intermediate stage of the three nitrotoluenes.

In the processes according to the state of the art the relative amount of the toluidine isomers was fixed within narrow limits due to the relatively inflexible mixture of the three nitrotoluene isomers.

The following examples illustrate the invention.

EXAMPLE 1

ZSM-5, a synthetic zeolite of the pentasil type was prepared according to known methods, for example according to British Pat. No. 1,567,948, and after addition of 20 weight % of $Al_2O_3$ as binder, extruded to corresponding specimens, dried for 12 hours at 120° C. and calcined for 4 hours at a temperature of from 400° to 500° C. Ion exchange was subsequently carried out at about 100° C. under reflux conditions by means of aqueous 2N $NH_4NO_3$ solution, and the catalyst was then washed free from nitrate ions. After drying in a vacuum drying cabinet at about 100° C., the $NH_4$—ZSM-5 was converted to the proton form by a five hours' calcination at 500°-550° C. 50 ml (about 27 g) of this catalyst having the shape of extruded specimens (5-10 mm × 1 mm) were arranged in a glass reactor as a packing having a height of about 190 mm and a diameter of 20 mm, and heated by an electric stove.

From a heated dropping funnel, 10 ml/h of o-toluidine (9.9 g = 92.5 mmols) were metered in together with 0.5 l/h of nitrogen. The isomerization mixture was condensed and analyzed by gas chromatography.

At a reaction temperature of 350° C., the isomer mixture consisted of 67.3 mol % of o-toluidine, 26.3 mol % of m-toluidine and 6.4 mol % of p-toluidine after a reaction time of 5-6 hours. After the temperature had been raised to 400° C. and a total reaction time of 48-56 hours, the composition of the isomer mixture was as follows: 69.3 mol % of o-toluidine, 22.9 mol % of m-toluidine and 7.7 mol % of p-toluidine. After a total reaction time of 88 hours the corresponding mol percentages of the toluidine isomers were 81.3, 13.9 and 4.8, respectively. By controlled burning of the catalyst with oxygen-containing gases its initial activity was restored.

EXAMPLE 2

A ZSM-5 catalyst was prepared as indicated in Example 1, but in this case (instead of exchange with NH₄NO₃) converted to the H—ZSM-5 form by treatment with 2N HCl for 24 hours at 50°–100° C. After washing with water until there were no chlorine ions present any more, the zeolite was dried at 100° C. in a drying cabinet, and calcined for 5 hours at 400°–450° C.

Analogously to Example 1, an o-toluidine isomerization was carried out at 400° C. After a reaction time of 6 hours, the composition of the toluidine mixture was as follows: 38.4 mol % of o-, 44.0 mol % of m- and 15.7 mol % of p-toluidine. Small amounts of aniline were detected in addition.

When p-toluidine was passed over the catalyst in analogous manner, the isomer composition after 16 hours at 400° C. was 18.6 mol % of o-, 50.4 mol % of m- and 29.2 mol % of p-toluidine.

When instead of p-toluidine m-toluidine was passed over the catalyst having been used as indicated before, the isomer composition after a further 4 hours, that is, a total reaction time of 20 hours, was 10.6 mol % of o-, 71.3 mol % of m- and 17.6 mol % of p-toluidine.

EXAMPLES 3 TO 6

ZSM-5 zeolites were converted to the didymium[1], ammonium, sodium or beryllium form by exchange with the corresponding nitrates, washed, dried and calcined. The Table indicates the results of tests in which first o-toluidine was passed over the catalyst for 6 hours, and then p-toluidine for 6 hours, too. The temperature was 400° C.

[1]didymium=commercial mixture of rare earths consisting of lanthanum, cerium, praseodymium, neodymium and small amounts of samarium, gadolinium, ytterbium etc.

TABLE

| Catalyst | Starting-material | Catalyst age (h) | o-toluidine | m-toluidine (mol %) | p-toluidine |
| --- | --- | --- | --- | --- | --- |
| Di—ZSM-5 | o-toluidine | 6 | 39.6 | 43.3 | 14.9 |
| " | p-toluidine | 12 | 10.6 | 52.4 | 33.2 |
| NH₄—ZSM-5 | o-toluidine | 6 | 35.0 | 46.3 | 16.4 |
| " | p-toluidine | 12 | 6.4 | 46.6 | 42.8 |
| Na—ZSM-5 | o-toluidine | 6 | 48.7 | 37.9 | 13.3 |
| " | p-toluidine | 12 | 18.3 | 59.1 | 22.6 |
| Be—ZSM-5 | o-toluidine | 6 | 46.6 | 38.9 | 14.3 |
| " | p-toluidine | 12 | 4.1 | 34.6 | 55.5 |

What is claimed is:

1. A process for the manufacture of at least one member selected from the group consisting of o-toluidine m-toluidine and p-toluidine, which comprises
    (a) treating, at a temperature of from 250° to 500° C., a first charge containing at least one toluidine isomer other than a toluidine isomer sought to be isolated, with an isomerization catalyst selected from the group of synthetic zeolites of the pentasil type, the ions of which are exchanged, to form a second charge,
    (b) isolating the desired toluidine isomer from the second charge by selective adsorption to an X or Y zeolite, the ions of which are exchanged, and subsequent desorption, and
    (c) recycling the balance of the second charge to step (a).

2. A process as recited in claim 1, wherein the temperature of the treating step is from 300° to 450° C.

3. A process as recited in claim 1, wherein the exchanged ions are cations selected from the group consisting of Na(+), H(+), NH₄(+), Be²(+), Mg²(+), Ca²(+) and rare earth metal ions, or combinations of these cations.

4. A process for the manufacture of at least one member selected from the group consisting of o-toluidine, m-toluidine and p-toluidine, which comprises
    (a) treating, at a temperature of from 250° to 500° C., a first charge containing at least one toluidine isomer other than a toluidine isomer sought to be isolated, with an isomerization catalyst selected from the group of synthetic zeolites of the X or Y type, the ions of which are exchanged, to form a second charge,
    (b) isolating the desired toluidine isomer from the second charge by selective adsorption to an X or Y zeolite, the ions of which are exchanged, and subsequent desorption, and
    (c) recycling the balance of the second charge to step (a).

5. A process as recited in claim 4, wherein the temperature of the treating step is from 300° to 450° C.

6. A process as recited in claim 4, wherein the exchanged ions are cations selected from the group consisting of Na(+), N(+), NH₄(+), Be²(+), Mg²(+), Ca²(+) and rare earth metal ions, or combinations of these cations.

7. A process for the manufacture of at least one member from the group consisting of o-toluidine, m-toluidine and p-toluidine, which comprises
    (c) isolating a desired toluidine isomer from a first charge by selective adsorption to an X or Y zeolite, the ions of which are exchanged, and subsequent desorption,
    (d) treating, at a temperature of from 250° to 500° C., the balance of the first charge with an isomerization catalyst selected from the group of synthetic zeolites of the pentasil type, the ions of which are exchanged, to form a second charge, and
    (e) recycling the second charge to step (c).

8. A process as recited in claim 7, wherein the temperature of the treating step is from 300° to 450° C.

9. A process as recited in claim 7, wherein the exchanged ions are cations selected from the group consisting of Na(+), H(+), NH₄(+), Be²(+), Mg²(+), Ca²(+) and rare earth metal ions, or combinations of these cations.

10. A process for the manufacture of at least one member from the group consisting of o-toluidine, m-toluidine and p-toluidine, which comprises
    (c) isolating a desired toluidine isomer from a first charge by selective adsorption to an X or Y zeolite, the ions of which are exchanged, and subsequent desorption,
    (d) treating, at a temperature of from 250° to 500° C., the balance of the first charge with an isomerization catalyst selected from the group of synthetic zeolites of the X or Y type, the ions of which are exchanged, to form a second charge, and
    (e) recycling the second charge to step (c).

11. A process as recited in claim 10, wherein the temperature of the treating step is from 300° to 450° C.

12. A process as recited in claim 10, wherein the exchanged ions are cations selected from the group consisting of Na(+), H(+), NH₄(+), Be²(+), Mg²(+), Ca²(+) and rare earth metal ions, or combinations of these cations.

* * * * *

UNITED STATES PATENT AND TRADEMARK OFFICE
CERTIFICATE OF CORRECTION

PATENT NO. : 4,480,128
DATED : October 30, 1984
INVENTOR(S) : Hans-Jurgen Arpe, Heinz Litterer It is certified that error appears in the above-identified patent and that said Letters Patent is hereby corrected as shown below:

In the Claims:

Claim 6, line 3 (column 6, line 23), change "$N^{(+)}$" to -- $H^{(+)}$ --.

Signed and Sealed this

Sixteenth Day of July 1985

[SEAL]

*Attest:*

DONALD J. QUIGG

*Attesting Officer*  *Acting Commissioner of Patents and Trademarks*